(12) United States Patent
Swiss et al.

(10) Patent No.: US 11,480,577 B2
(45) Date of Patent: *Oct. 25, 2022

(54) BIOPSY METHODS AND DEVICES

(71) Applicant: Indicator Systems International, Inc., Newport Beach, CA (US)

(72) Inventors: Gerald F. Swiss, Rancho Santa Fe, CA (US); John V. Fante, Newport Beach, CA (US); Robert M. Moriarty, Michiana Shores, IN (US); Richard J. Pariza, Zion, IL (US)

(73) Assignee: INDICATOR SYSTEMS INTERNATIONAL, INC., Newport Beach, CA (US)

( * ) Notice: Subject to any disclaimer, the term of this patent is extended or adjusted under 35 U.S.C. 154(b) by 285 days.

This patent is subject to a terminal disclaimer.

(21) Appl. No.: 16/740,027

(22) Filed: Jan. 10, 2020

(65) Prior Publication Data

US 2020/0150127 A1    May 14, 2020

Related U.S. Application Data

(63) Continuation of application No. 15/595,860, filed on May 15, 2017, now Pat. No. 10,539,567.

(51) Int. Cl.
| | | |
|---|---|---|
| *A61B 10/02* | (2006.01) | |
| *C07D 519/00* | (2006.01) | |
| *G01N 33/58* | (2006.01) | |
| *C12Q 1/44* | (2006.01) | |
| *G01N 33/574* | (2006.01) | |
| *A61B 10/00* | (2006.01) | |

(52) U.S. Cl.
CPC ....... *G01N 33/582* (2013.01); *A61B 10/0096* (2013.01); *A61B 10/0233* (2013.01); *C07D 519/00* (2013.01); *C12Q 1/44* (2013.01); *G01N 33/57492* (2013.01)

(58) Field of Classification Search
CPC .......... G01N 33/582; G01N 33/57492; C07D 519/00; A61B 10/0096; A61B 10/0233; C12Q 1/44
See application file for complete search history.

(56) References Cited

U.S. PATENT DOCUMENTS 8,420,396 B2 *    4/2013    Uhlmann ................ A61P 35/00
435/375

OTHER PUBLICATIONS

Dam et al. Intraoperative tumor-specific fluorescence imaging in ovarian cancer by folate receptor-alpha targeting: first in-human results. Nature Medicine 2011, vol. 17, No. 10, pp. 1315-1320. (Year: 2011).*

Robertson et al. Fluorescein Derivatives in Intravital Fluorescence Imaging. Cells 2013, vol. 2, pp. 591-606; (Year: 2013).*

* cited by examiner

*Primary Examiner* — Shafiqul Haq

(74) *Attorney, Agent, or Firm* — Procopio, Cory, Hargreaves & Savitch LLP

(57) ABSTRACT

Disclosed are methods for detecting remnant cancer cells in a tissue sample.

3 Claims, 1 Drawing Sheet

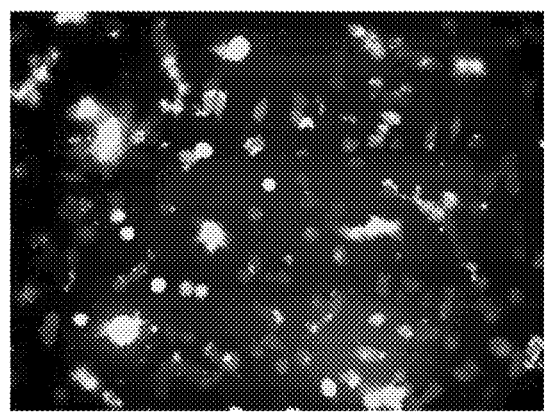

BIOPSY METHODS AND DEVICES

RELATED APPLICATION

This application is a continuation application of U.S. patent application Ser. No. 15/595,860, entitled "Biopsy Methods and Devices", filed May 15, 2017, which is hereby incorporated by reference in its entirety.

FIELD OF THE INVENTION

This invention is directed to methods and devices for conducting tissue biopsies.

STATE OF THE ART

Current biopsy methods typically involve obtaining a tissue sample via a biopsy needle, forwarding the sample for evaluation, obtaining an analysis of the sample and then communicating with the patient as to the results. In 2009, it was reported by the New York Times that the average wait time to receive the results was reported to be 2.5 days with some patients waiting 10 days or more. Currently, it is estimated that over 1.6 million breast biopsies are performed annually with only about 20% providing a cancer diagnosis. In addition, biopsies are often conducted to determine a diagnosis for other solid masses that may be cancerous such as those conducted for liver masses, lung masses, etc. The shear number of such biopsies conducted invariably leads to delays during which the patients are left with a traumatic period of not knowing their results.

In view of the above, it would be advantageous if biopsy methods could immediately provide the doctor with a result that could be conveyed to the patient.

SUMMARY OF THE INVENTION

This invention is directed to the methods and devices for conducting biopsies where excised tissue samples comprising viable cells are immediately evaluated for a positive or negative result for cancer. Such methods and devices allow the physician to advise the patient of the results even if such results were considered preliminary in nature.

Accordingly, in one embodiment, this invention is directed to a method for detecting the presence or absence of cancer cells in an excised cellular mass comprising viable cells which are suspected of including cancer cells which method comprises:

excising a cellular mass from a patient and placing said mass into a suitable medium to maintain viability of cells in said mass;

contacting said mass with a conjugate comprising a tumor targeting component and a pro-detection component so that the conjugate selectively binds to and is then absorbed by any cancer cells in said mass whereupon the pro-detection component is intracellularly converted into a detection component with a signaling fingerprint;

optionally washing said mass to remove any unbound conjugate;

evaluating the contacted mass for signal generated from the detection component of said conjugate; and correlating the presence or absence of said signal fingerprint so as to assess the presence or absence of cancer cells.

In one embodiment, the methods of this invention employ a conjugate of formula I:

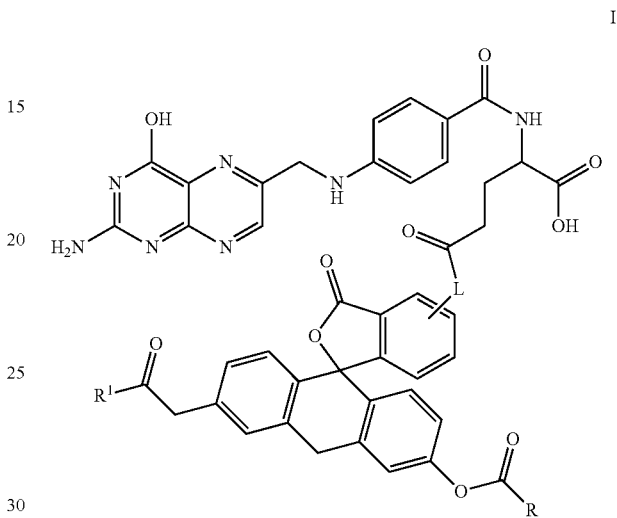

I wherein said compound selectively attaches to and is absorbed by cancer cells and is then intracellularly converted into a fluorescent compound with a fluorescent fingerprint; and further wherein R and $R^1$ are independently $C_2$-$C_{18}$ alkyl or cycloalkyl groups either or both optionally containing 1 to 8 heteroatoms selected from the group consisting of oxygen, $S(O)_x$, $>NR^3$, $-OP(O)_yH$, $-OS(O)_zH$, $-C(O)-$, amino, $C_1$-$C_6$ alkylamino, di($C_1$-$C_6$ dialkyl)amino, $-C(O)$ $O-$, $-C(O)NR^3-$, $-C(O)OH$, $-OH$, and oxo wherein y and z are independently 1 or 2, and x is 0, 1 or 2;

$R^3$ is hydrogen or $C_1$-$C_6$ alkyl; and

L is a linker of from 1 to 20 carbon atoms and 1 to 6 heteroatoms selected from the group consisting of oxygen, $S(O)_x$, $>NR^3$, $-OP(O)_yH$, $-OS(O)_zH$, $-C(O)-$, amino, $C_1$-$C_6$ alkylamino, di($C_1$-$C_6$ dialkyl)amino, $-C(O)O-$, $-C(O)NR^3-$, $-C(O)OH$, $-OH$, and oxo wherein y and z are independently 1 or 2, and x is 0, 1 or 2;

or pharmaceutically acceptable salts and/or solvates thereof.

In one embodiment, the methods of this invention employ a conjugate of formula II:

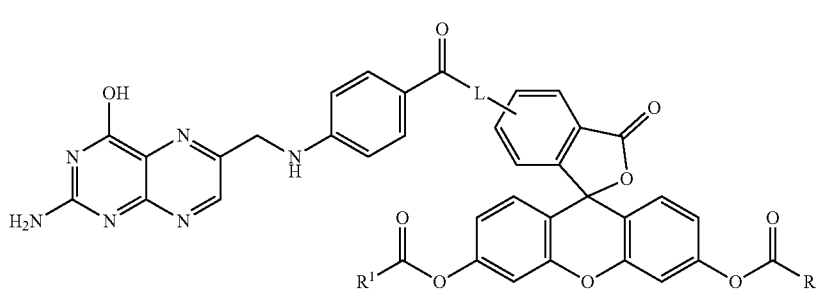

II wherein said compound selectively attaches to and is absorbed by cancer cells and is then intracellularly converted into a fluorescent compound with a fluorescent fingerprint; and further wherein R and $R^1$ are independently $C_2$-$C_{18}$ alkyl or cycloalkyl groups either or both optionally containing 1 to 8 heteroatoms selected from the group consisting of oxygen, $S(O)_x$, $>NR^3$, —$OP(O)_yH$, —$OS(O)_zH$, —C(O)—, amino, $C_1$-$C_6$ alkylamino, di($C_1$-$C_6$ dialkyl)amino, —C(O)O—, —C(O)$NR^3$—, —C(O)OH, —OH, and oxo wherein y and z are independently 1 or 2, and x is 0, 1 or 2;

$R^3$ is hydrogen or $C_1$-$C_6$ alkyl; and

L is a linker of from 1 to 20 carbon atoms and 1 to 6 heteroatoms selected from the group consisting of oxygen, $S(O)_x$, $>NR^3$, —$OP(O)_yH$, —$OS(O)_zH$, —C(O)—, amino, $C_1$-$C_6$ alkylamino, di($C_1$-$C_6$ dialkyl)amino, —C(O)O—, —C(O)$NR^3$—, —C(O)OH, —OH, and oxo wherein y and z are independently 1 or 2, and x is 0, 1 or 2;

or pharmaceutically acceptable salts and/or solvates thereof.

In one embodiment, the methods of this invention employ a conjugate of formula III:

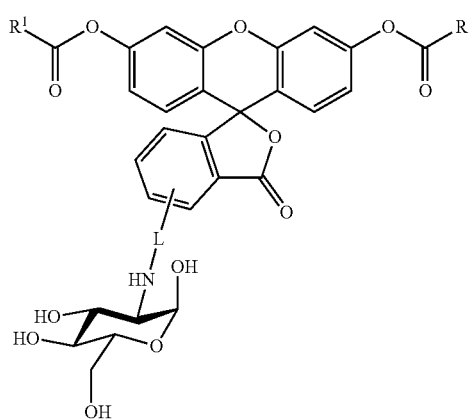

III wherein said compound selectively attaches to and is absorbed by cancer cells and is then intracellularly converted into a fluorescent compound with a fluorescent fingerprint; and further wherein R and $R^1$ are independently $C_2$-$C_{18}$ alkyl or cycloalkyl groups either or both optionally containing 1 to 8 heteroatoms selected from the group consisting of oxygen, $S(O)_x$, $>NR^3$, —$OP(O)_yH$, —$OS(O)_zH$, —C(O)—, amino, $C_1$-$C_6$ alkylamino, di($C_1$-$C_6$ dialkyl)amino, —C(O)O—, —C(O)$NR^3$—, —C(O)OH, —OH, and oxo wherein y and z are independently 1 or 2, and x is 0, 1 or 2;

$R^3$ is hydrogen or $C_1$-$C_6$ alkyl; and

L is a linker of from 1 to 20 carbon atoms and 1 to 6 heteroatoms selected from the group consisting of oxygen, $S(O)_x$, $>NR^3$, —$OP(O)_yH$, —$OS(O)_zH$, —C(O)—, amino, $C_1$-$C_6$ alkylamino, di($C_1$-$C_6$ dialkyl)amino, —C(O)O—, —C(O)$NR^3$—, —C(O)OH, —OH, and oxo wherein y and z are independently 1 or 2, and x is 0, 1 or 2;

or pharmaceutically acceptable salts and/or solvates thereof.

In one embodiment, this invention provides for a kit of parts comprising a biopsy needle and a chamber capable of receiving the biopsied tissue. In this embodiment, the chamber is separated from the needle and is capable of holding a solution comprising a conjugate of this invention in a medium suitable for maintaining the viability of cells in said mass. The chamber itself is otherwise substantially non-fluorescent. The kit of parts optionally comprises a container comprising a conjugate of this invention either in solution or as a solid. When employed as a solid, a separate container comprising a suitable solution can optionally be included in the kit of parts.

In one embodiment, this invention provides for a devise comprising a biopsy needle and a chamber capable of receiving the biopsied tissue wherein the needle and chamber are integrated into the device so that the tissue sample is fed directly from the needle into the chamber. The chamber is capable of holding a solution comprising a conjugate of this invention in a medium suitable for maintaining the viability of cells in said mass. The chamber itself is otherwise substantially non-fluorescent. In one preferred option, the chamber is equipped with an external UV source and a camera capable of recording fluorescence.

In one embodiment, the solution employed with either the kit of parts or the device comprises from about 50 to about 95 weight percent of the aqueous composition and a co-solvent that comprises from about 5 to about 50 weight percent of the aqueous composition. In one embodiment, the co-solvent is DMSO.

In one embodiment, this invention is directed to a method for detecting cancer cells in a tissue sample suspected of containing such cells wherein said method comprises:

excising a tissue sample from a patient wherein said sample comprises viable cells suspected of being cancerous;

placing said excised sample in a chamber;

adding to said chamber a sufficient amount of a sterile aqueous composition comprising a water-soluble fluorescein diester of formula I, II or III wherein said aqueous composition contacts said sample and optionally comprises up to 50 percent by weight of a water soluble or miscible and biologically compatible co-solvent and further wherein said composition maintains the viability of cells within said mass;

maintaining said contact for a sufficient period of time to permit absorption of said diester and intracellular deacylation thereof by said cancer cells if present;

optionally washing said surface with a sterile aqueous solution free of any of said diester(s); and assessing the presence of intracellular fluorescence in said cellular mass as an indicia of the presence of cancer cells in said mass.

Specific compounds as well as salts and solvates of formula I of this invention include the following (left side of L is attached to folic acid):

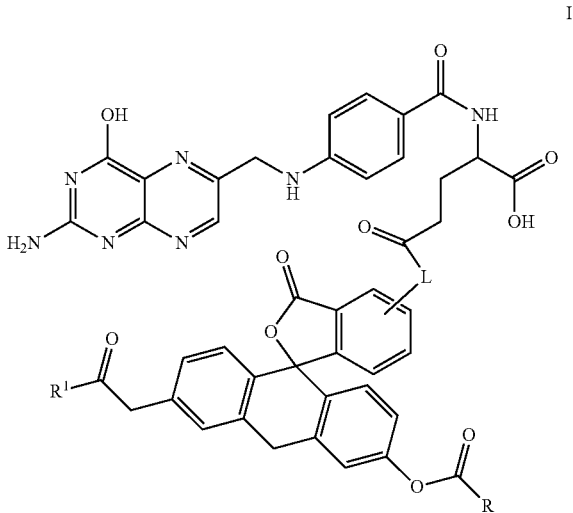

I

| # | R/R¹ | R² | L |
|---|------|-----|---|
| 1 | $CH_3OCH_2CH_2OC(O)CH_2CH_2C(O)O-$ / $CH_3OCH_2CH_2OC(O)CH_2CH_2C(O)O-$ | H | —NH—C(=S)(NH)—NH— (via CH, thiourea linker) |
| 2 | $CH_3OCH_2CH_2OC(O)CH_2CH_2C(O)O-$ / $CH_3OCH_2CH_2OC(O)CH_2CH_2C(O)O-$ | $CH_3$ | —NH—CH₂—C₆H₄—NH—C(=S)—NH— |
| 3 | $CH_3OCH_2CH_2OC(O)CH_2CH_2C(O)O-$ / $CH_3OCH_2CH_2OC(O)CH_2CH_2C(O)O-$ | H | $-NHCH_2CH_2CH_2(OCH_2CH_2)_3CH_2NHC(=S)NH-$ |
| 4 | $CH_3OCH_2CH_2OC(O)CH_2CH_2C(O)O-$ / $CH_3OCH_2CH_2OC(O)CH_2CH_2C(O)O-$ | H | —NHCH₂CH₂NH— |
| 5 | $CH_3OCH_2CH_2OC(O)CH_2CH_2C(O)O-$ / $CH_3OCH_2CH_2OC(O)CH_2CH_2C(O)O-$ | H | —NHCH₂CH₂CH₂NH— |
| 6 | $CH_3OCH_2CH_2OC(O)CH_2CH_2C(O)O-$ / $CH_3CH_2C(O)O-$ | H | —NH—C₆H₄—CH₂—NH—C(=S)—NH— |
| 7 | $CH_3O_2C(CH_2CH_2O)_3C(O)(CH_2CH_2O)_3C(O)O-$ / $CH_3O_2C(CH_2CH_2O)_3C(O)(CH_2CH_2O)_3C(O)O-$ | H | —NH—C₆H₄—CH₂—NH—C(=S)—NH— |
| 8 | $CH_3O(CH_2CH_2O)_2CH_2C(O)O-$ / $CH_3O(CH_2CH_2O)_2CH_2C(O)O-$ | H | —NH—CH—NH—C(=S)—NH— |

Specific compounds as well as salts and solvates of formula I of this invention include the following (left side of L is attached to pteroic acid):

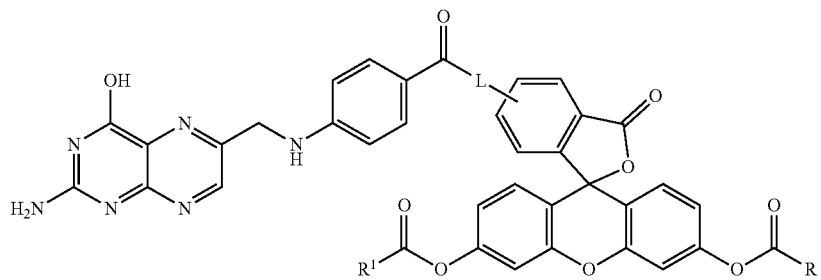

II

| No. | R/R¹ | L |
|---|---|---|
| 9 | CH₃OCH₂CH₂OC(O)CH₂CH₂C(O)O—/<br>CH₃OCH₂CH₂OC(O)CH₂CH₂C(O)O— | —NH—C(=S)—NH— (via CH₂: —NH—CH₂—NH—C(=S)—NH—) |
| 10 | CH₃OCH₂CH₂OC(O)CH₂CH₂C(O)O—/<br>CH₃OCH₂CH₂OC(O)CH₂CH₂C(O)O— | —NH—CH₂—C₆H₄—NH—C(=S)—NH— |
| 11 | CH₃OCH₂CH₂OC(O)CH₂CH₂C(O)O—/<br>CH₃OCH₂CH₂OC(O)CH₂CH₂C(O)O— | —NH—C₆H₄—CH₂—NH—C(=S)—NH— |
| 12 | CH₃OCH₂CH₂OC(O)CH₂CH₂C(O)O—/<br>CH₃OCH₂CH₂OC(O)CH₂CH₂C(O)O— | —NHCH₂CH₂NH— |
| 13 | CH₃OCH₂CH₂OC(O)CH₂CH₂C(O)O—<br>CH₃OCH₂CH₂OC(O)CH₂CH₂C(O)O— | —NHCH₂CH₂NH— |
| 14 | CH₃OCH₂CH₂OC(O)CH₂CH₂C(O)O—/<br>CH₃CH₂C(O)O— | —NH—C(=S)—NH—CH₂—C₆H₄—NH— |
| 15 | CH₃O₂C(CH₂CH₂O)₃C(O)(CH₂CH₂O)₃C(O)O— | —NH—C(=S)—NH—CH₂—C₆H₄—NH— |
| 16 | CH₃O(CH₂CH₂O)₄CH₂CH₂C(O)O—/<br>CH₃O(CH₂CH₂O)₄CH₂CH₂C(O)O— | —NH—CH₂—NH—C(=S)—NH— |

Specific compounds and salts/solvates of formula I of this invention include the following (left side of L is attached to the nitrogen of glucosamine):

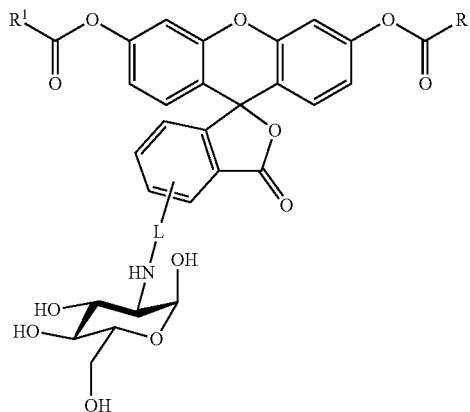

| Compound No. | R/R$^1$ | L |
|---|---|---|
| 17 | CH$_3$OCH$_2$CH$_2$OC(O)CH$_2$CH$_2$C(O)—/<br>CH$_3$OCH$_2$CH$_2$OC(O)CH$_2$CH$_2$C(O)— | —C(=S)NH— |
| 18 | CH$_3$OCH$_2$CH$_2$OC(O)CH$_2$CH$_2$C(O)—/<br>CH$_3$OCH$_2$CH$_2$OC(O)CH$_2$CH$_2$C(O)— | —CH$_2$CH$_2$CH$_2$NHC(=S)NH— |
| 19 | CH$_3$OCH$_2$CH$_2$OC(O)CH$_2$CH$_2$C(O)—/<br>CH$_3$OCH$_2$CH$_2$OC(O)CH$_2$CH$_2$C(O)— | —CH$_2$NHC(=S)NH— |
| 20 | CH$_3$OCH$_2$CH$_2$OC(O)CH$_2$CH$_2$C(O)—/<br>CH$_3$OCH$_2$CH$_2$OC(O)CH$_2$CH$_2$C(O)— | —CH$_2$CH$_2$NHC(=S)NH— |
| 21 | CH$_3$OCH$_2$CH$_2$OC(O)CH$_2$CH$_2$C(O)—/<br>CH$_3$OCH$_2$CH$_2$OC(O)CH$_2$CH$_2$C(O)— | —CH$_2$CH$_2$NHC(=O)NH— |
| 22 | CH$_3$OCH$_2$CH$_2$OC(O)CH$_2$CH$_2$C(O)—/<br>CH$_3$CH$_2$C(O)— | —C(=S)NH— |
| 23 | CH$_3$O$_2$C(CH$_2$CH$_2$O)$_3$C(O)(CH$_2$CH$_2$O)$_3$C(O)— | —C(=S)NH— |
| 24 | CH$_3$O(CH$_2$CH$_2$O)$_4$CH$_2$CH$_2$C(O)—/<br>CH$_3$O(CH$_2$CH$_2$O)$_4$CH$_2$CH$_2$C(O)— | CH$_2$NHC(=S)NH— |
| 25 | R & R$^1$ = 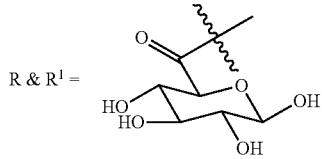<br>Glucuronic acid derivative | —CH$_2$CH$_2$NHC(=S)NH— |

In one preferred embodiment, the compounds of this invention when converted to their fluorescent form are capable of maintaining a fluorescent signal for at least 5 minutes and preferably at least 10 minutes after exposure to UV light. In addition, the resulting fluorescent compounds of this invention preferably do not efflux from the cells back into the solution. Still further, the compounds of formula I and II are particularly suited for detecting epithelial cancer cells, ovarian cancer cells, cervical cancer cells, breast cancer cells, lung cancer cells, kidney cancer cells, colorectal cancer cells, and brain cancer cells.

BRIEF DESCRIPTION OF THE DRAWING

FIG. 1 illustrates the intra-cellular generation of fluorescence of cancer cells that have absorbed a conjugate of this invention and then intracellularly deacylated said conjugate.

DETAILED DESCRIPTION OF THE INVENTION

As noted above, this invention provides for a method for detecting the presence or absence of cancer cells in an excised cellular mass suspected of containing cancer cells. However, prior to providing a detailed description of the several aspects of this invention, the following terms will first be defined.

Definitions

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of this invention. Procedures for inserting such labels into the compounds of this invention will be readily apparent to those skilled in the art based on the disclosure herein.

The term "cancer", "solid mass cancers or tumors" and "cancer cells" refer to cancer cells that form solid masses and as such blood borne cancers are not included within these terms. Also, the term "maintaining the viability of such cells" or language equivalent thereto means that the cells remain viable for a sufficient period of time such that a conjugate comprising a tumor targeting component and a pro-detection component selectively binds to and is then absorbed by any cancer cells in said mass whereupon the pro-detection component is intracellularly converted into a detection component with a signaling fingerprint. Preferably, such a period of time is at least 1 minute, more preferably, at least 5 minutes. Particularly preferred ranges include from 1 to 20 minutes and 5 to 15 minutes.

It is also generally recognized that in many but not all cancers, their rapid growth requires preferential uptake of folic acid (a nucleoside precursor). As such, the term "folic acid requiring cancer cells" refer to those cancer cells that over-express the folic acid receptor which is some cases is up to as many as 8-10 times that of normal cells. Cancer cells recognized to require folic acid and, therefore, have an excess of folic acid receptors include, but are not limited to, epithelial cancer cells, ovarian cancer cells, cervical cancer cells, breast cancer cells, lung cancer cells, kidney cancer cells, colorectal cancer cells, and brain cancer cells. Likewise, it is generally recognized that in order to keep up with the high nutritional and energy needs of a malignant tumor, cancer cells show a 20- to 30-fold higher rate of glucose uptake and glycolysis compared with normal cells. Hence, the use of sugars that are recognized by the glucose receptors on malignant tumor cells provide one route to conjugate the pro-detectible label and have the conjugate formed thereby preferentially taken up by these cancer cells. Accordingly, with compounds of formula III as well as those having a different sugar components that are recognized by one or more of the glucose receptors (e.g., glucosamine and fructose), all solid mass tumor cells that require high glucose uptake are suitable for identification by the methods of this invention.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, aminocarbonyl, aminocarbonylamino, aminocarbonyloxy, acyloxy, aryl, substituted aryl, arylene, substituted arylene, heteroarylene, substituted heteroarylene, aryloxy, substituted aryloxy, carboxyl, carboxyl ester, cyano, cycloalkyl, cycloalkylene, substituted cycloalkyl, substituted cycloalkylene, cycloalkyloxy, substituted cycloalkyloxy, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, oxo, and $SO_3H$.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl).

"Acyl" refers to the groups H—C(O)—, alkyl-C(O)—, substituted alkyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—. Acyl includes the "acetyl" group $CH_3C(O)$—.

"Acylamino" refers to —$NR^{47}C(O)$alkyl, —$NR^{47}C(O)$ substituted alkyl, —$NR^{47}C(O)$cycloalkyl, —$NR^{47}C(O)$substituted cycloalkyl, —$NR^{47}C(O)$aryl, —$NR^{47}C(O)$substituted aryl, —$NR^{47}C(O)$heteroaryl, —$NR^{47}C(O)$substituted heteroaryl, —$NR^{47}C(O)$heterocyclic, and —$NR^{47}C(O)$substituted heterocyclic wherein $R^{47}$ is hydrogen or alkyl.

"Acyloxy" refers to the groups alkyl-C(O)O—, substituted alkyl-C(O)O—, aryl-C(O)O—, substituted aryl-C(O) O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O.

"Aminocarbonyl" refers to the group —$C(O)NR^{50}R^{51}$ where $R^{50}$ and $R^{51}$ are independently selected from the group consisting of hydrogen, alkyl, substituted alkyl, aryl, substituted aryl, cycloalkyl, substituted cycloalkyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group.

"Aminocarbonylamino" refers to the group —$NR^{47}C(O)$ $NR^{50}R^{51}$ where $R^{47}$ is hydrogen or alkyl and $R^{50}$ and $R^{51}$ are independently selected from the group consisting of hydrogen, alkyl, substituted alkyl, aryl, substituted aryl, cycloalkyl, substituted cycloalkyl, heteroaryl, substituted heteroaryl, heterocyclic, and substituted heterocyclic, and where $R^{50}$ and $R^{51}$ are optionally joined together with the nitrogen bound thereto to form a heterocyclic or substituted heterocyclic group.

"Aminocarbonyloxy" refers to the group —O—C(O) $NR^{50}R^{51}$ where $R^{50}$ and $R^{51}$ are independently selected from the group consisting of hydrogen, alkyl, substituted alkyl, aryl, substituted aryl, cycloalkyl, substituted cycloalkyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkoxy, substituted alkoxy, acyl, acylamino, acyloxy, aminocarbonyl, aminocarbonylamino, aminocarbonyloxy, aryl, substituted aryl, aryloxy, substituted aryloxy, carboxyl, carboxyl ester, cyano, cycloalkyl, substituted cycloalkyl, cycloalkyloxy, substituted cycloalkyloxy, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, and $SO_3H$.

"Arylene" refers to a divalent aromatic carbocyclic group of from 6 to 14 carbon atoms having a single ring or multiple condensed rings. "Substituted arylene" refers to an arylene having from 1 to 5, preferably 1 to 3, or more preferably 1 to 2 substituents as defined for aryl groups.

"Heteroarylene" refers to a divalent aromatic group of from 1 to 10 carbon atoms and 1 to 4 heteroatoms selected from the group consisting of oxygen, nitrogen and sulfur within the ring. "Substituted heteroarylene" refers to heteroarylene groups that are substituted with from 1 to 5, preferably 1 to 3, or more preferably 1 to 2 substituents selected from the group consisting of the same group of substituents defined for substituted aryl.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the group —C(O)(O)-alkyl, —C(O)(O)-substituted alkyl, —C(O)(O)-aryl, —C(O)(O)-substituted-aryl, —C(O)(O)-cycloalkyl, —C(O)(O)-substituted cycloalkyl, —C(O)(O)-heteroaryl, —C(O)(O)-substituted heteroaryl, —C(O)(O)-heterocyclic, and —C(O)(O)-substituted heterocyclic.

"Oxycarbonyl esters" refer to the group "acyloxy" as defined above.

In a preferred embodiment, such ester groups contain 2 to 18 carbon atoms and optionally contain from 1 to 6 heteroatoms selected from the group consisting of oxygen, $S(O)_x$, $NR^3$, $—OP(O)_yH$, $—OS(O)_zH$ wherein y and z are independently 1 or 2, and x is 0, 1 or 2 whereby such substitutions impart improved water solubility or maintain water-solubility for the compound to which they are attached.

"Cyano" refers to the group —CN.

"Cycloalkyl" refers to cyclic alkyl groups of from 3 to 10 carbon atoms having single or multiple cyclic rings including fused, bridged, and spiro ring systems. The fused ring can be an aryl ring provided that the non-aryl part is joined to the rest of the molecule. Examples of suitable cycloalkyl groups include, for instance, adamantyl, cyclopropyl, cyclobutyl, cyclopentyl, and cyclooctyl.

"Substituted cycloalkyl" and "substituted cycloalkenyl" refers to a cycloalkyl or cycloalkenyl group having from 1 to 5 or preferably 1 to 3 substituents selected from the group consisting of oxo, alkyl, substituted alkyl, alkoxy, substituted alkoxy, acyl, acylamino, acyloxy, aminocarbonyl, aminocarbonylamino, aminocarbonyloxy, aryl, substituted aryl, aryloxy, substituted aryloxy, carboxyl, carboxyl ester, cyano, cycloalkyl, substituted cycloalkyl, cycloalkyloxy, substituted cycloalkyloxy, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, and $SO_3H$.

"Cycloalkylene" refers to a divalent cycloalkyl group and "substituted cycloalkylene" refers to a divalent substituted cycloalkyl group.

"Cycloalkyloxy" refers to —O-cycloalkyl.

"Substituted cycloalkyloxy refers to —O-(substituted cycloalkyl).

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Certain non-limiting examples include pyridinyl, pyrrolyl, indolyl, thiophenyl, oxazolyl, thizolyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —$NO_2$.

"Oxo" refers to the atom (=O).

A substituted ring can be substituted with one or more fused and/or spiro cycles. Such fused cycles include a fused cycloalkyl, a fused heterocyclyl, a fused aryl, a fused heteroaryl ring, each of which rings can be unsubstituted or substituted. Such spiro cycles include a fused cycloalkyl and a fused heterocyclyl, each of which rings can be unsubstituted or substituted.

"Optionally substituted" refers to a group selected from that group and a substituted form of that group. Substituents are such as those defined hereinabove. In one embodiment, substituents are selected from $C_1$-$C_{10}$ or $C_1$-$C_6$ alkyl, substituted $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, $C_1$-$C_{10}$ heteroaryl, substituted $C_2$-$C_6$ alkenyl, substituted $C_2$-$C_6$ alkynyl, substituted $C_6$-$C_{10}$ aryl, substituted $C_3$-$C_8$ cycloalkyl, substituted $C_2$-$C_{10}$ heterocyclyl, substituted $C_1$-$C_{10}$ heteroaryl, halo, nitro, cyano, —$CO_2H$ or a $C_1$-$C_6$ alkyl ester thereof.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the substituents set forth herein and in the above definitions are not intended to include impermissible substitution patterns (e.g., methyl substituted with 5 fluoro groups). Such impermissible substitution patterns are well known to the skilled artisan.

"Tautomer" refer to alternate forms of a compound that differ in the position of a proton, such as enol/keto and imine/enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles. In the case of fluorescein, it exists in two tautomeric forms as shown below and each are covered by the term "fluorescein":

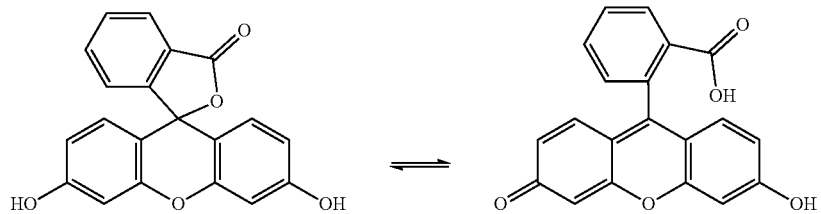 [SMILES: O=C1OC2(c3ccc(O)cc3Oc3cc(O)ccc32)c2ccccc21 ; O=C(O)c1ccccc1-c1c2ccc(=O)cc-2oc2cc(O)ccc12]

As used herein, the term stereochemically pure denotes a compound which has 80% or greater by weight of the indicated stereoisomer and 20% or less by weight of other stereoisomers. In a further embodiment, the compound of Formula (I), (II), or (III) has 90% or greater by weight of the stated stereoisomer and 10% or less by weight of other stereoisomers. In a yet further embodiment, the compound of Formula (I), (II), or (III) has 95% or greater by weight of the stated stereoisomer and 5% or less by weight of other stereoisomers. In a still further embodiment, the compound of formula (I), (II), or (III) has 97% or greater by weight of the stated stereoisomer and 3% or less by weight of other stereoisomers.

All terms not defined herein have their conventional definitions.

Synthesis

The compounds used in the methods of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

If the compounds contain one or more chiral centers, such compounds can be prepared or isolated as pure stereoisomers, i.e., as individual enantiomers or d(1) stereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001) and Larock's Comp. Organic Transformations (VCH Publishers Inc. 1989).

In one embodiment, the compounds used in the methods of this invention can be prepared from 5- or 6-thioisocyanate fluorescein by first acylating both phenolic hydroxyl groups as shown below:

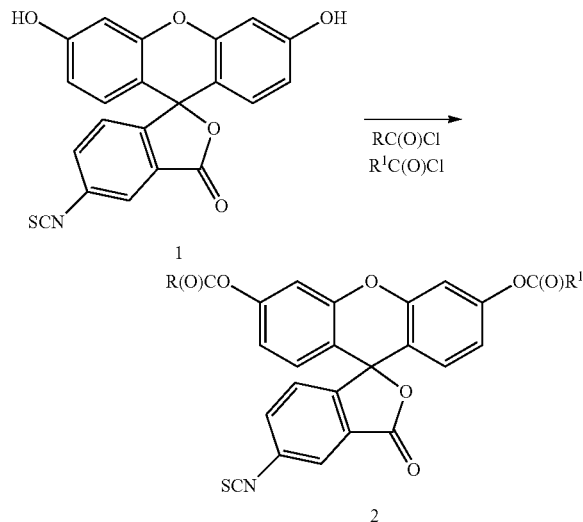

where R and R¹ are as defined herein. Compound 2 defines a class of novel intermediates within the scope of this invention.

In particular, compound 1 (5-isothiocyanate fluorescein) is contacted with at least two equivalents or more of a carboxyl acid chloride or other halide under esterifying conditions wherein each R and R¹ together with the carbonyl group —C(O)— is an acyl group as defined herein. The reaction is preferably conducted in a suitable aprotic inert diluent such as chloroform, ethyl acetate, methylene chloride and the like at a temperature of from about 0° to about 60° C. for a period of time sufficient to substantially complete the reaction. A suitable amount of a base such as triethylamine, diisopropylethylamine, and the like is typically added to scavenge the acid generated during the reaction. The product is typically isolated and purified by conventional techniques such as precipitation, crystallization, chromatography and the like.

Alternatively, as is well known in the art, compound 2 can be prepared by reaction with the corresponding acid anhydride [RC(O)OC(O)R] or mixed acid anhydride [RC(O)OC(O)R¹] by methods well known in the art. In addition, the isothiocyanate groups can be replaced with isocyanate, amino and haloacetamido groups all of which are commercially available as a fluorescein derivative and have the general structure:

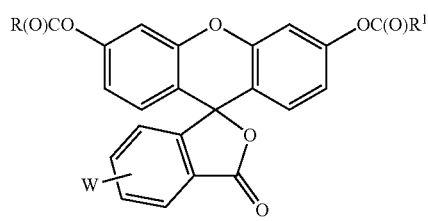

where R and R1 are as defined herein and W is a substituent selected from the group consisting of amino, haloacetamido, isocyanate, and thioisocyanate.

It is understood that the acyl groups selected are such that the resulting diester is soluble in an aqueous composition as defined herein. By "soluble", it is meant that the compound has sufficient solubility to provide detectible evidence of the presence of cancer cells when the fluorescein moiety is deacylated. In one preferred embodiment, solubility of at least 0.1 mg/mL in the aqueous composition at 25° C. and preferably at least 0.5 mg/mL is desireable.

Acyl groups that impart water solubility to the fluorescein diesters of this invention preferably comprise from 2 to 18 carbon atoms and from 1 to 12 heteroatoms such as oxygen. Suitable hydroxyl acyl groups include, by way of example only, $HOC(O)CH_2CH_2C(O)OCH_2CH_2OCH_3$ (compound 3), $CH_3OCH_2CH_2OCH_2CH_2OCH_2C(O)OH$ (compound 4), and $CH_3OCH_2CH_2OCH_2CH_2OCH_2CH_2OCH_2CH_2C(O)OH$ (compound 5). Compound 3 is a known compound prepared by reaction of succinic anhydride with approximately 1 equivalents of 2-methoxyethanol. The reaction proceeds via ring opening of the anhydride to provide for 3-(2-methoxyethoxy)carbonylproprionic acid. Compounds 4 and 5 are commercially available from Sigma-Aldrich, St. Louis, Mo., USA.

Synthetic schemes for the linkage of such soluble fluorescein derivatives to folic acid first proceeds via coupling of a linker to folic acid as shown in the following exemplary reaction scheme using a diamine linker:

In the case of folic acid, it is sometimes desirable to start with the folic acid anhydride. That compound can be prepared as per the procedures set forth in Guaranga, et al., Bioconjugate Chemistry, 2012, 23:84-96 which are incorporated herein by reference in their entirety.

In one embodiment, folic acid anhydride can be reacted with, e.g., $NH_2$-L-NHPg where Pg is a protecting group, L is a linker. One example of a suitable linker is >CH—$R^{10}$ where $R^{10}$ is an amino acid side chain. Another example of a suitable linker is a polyoxyalkylene group of the formula -(alkylene-O)$_p$— where p is from 1 to 20, and the like. Other examples of compounds suitable for linking the folic or pteroic acid to fluorescein diesters include $NH_2$-(alkylene-O)$_p$—H, 4-$H_2NCH_2$-aniline, 2-aminoethanol, and the like as illustrated in the reaction below.

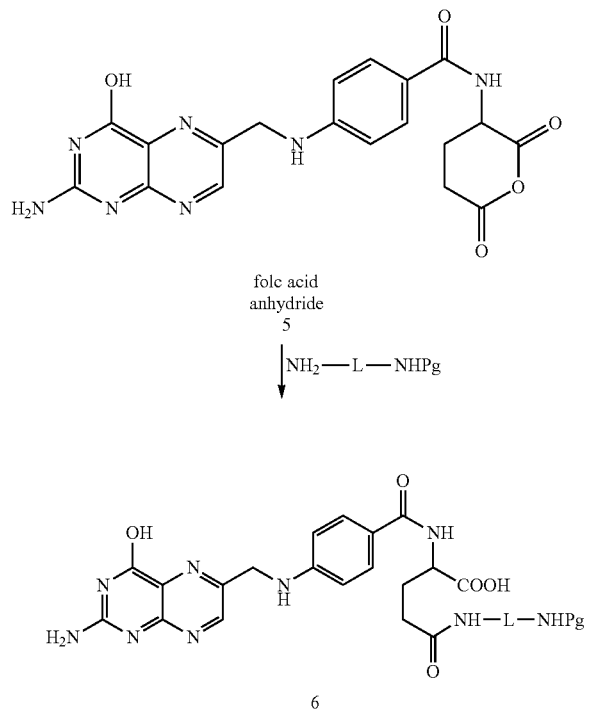

folic acid anhydride
5

$NH_2$—L—NHPg

6

The reaction proceeds under conventional amidation conditions and the resulting product, compound 6, is then isolated and purified by conventional methods or, alternatively used in the next step(s) without isolation and purification.

As to the next steps, the protecting group (Pg) is removed by conventional methods and the amino group is then free to react with the isothiocyanate group of compound 2. This reaction proceeds under conventional conditions and results in covalent linkage of the folic acid component or moiety to the fluorescein diester component or moiety through a thiourea bond.

Alternatively, 5-isothiocyanate fluorescein diesters can be reacted with pteroic acid in a similar manner as described above. In this reaction, the carboxyl group of pteroic acid is amidated with the $NH_2$-L-NHPg to form an amido-L-NHPg substituent. Again, the protecting group (Pg) is removed by conventional means. The resulting amino group then is reacted with the isothiocyanate group of the fluorescein diester to provide for the thiourea linkage of the pteroic acid component or moiety to the fluorescein diester component or moiety. Still further, glucose amine can be reacted directly with the 5-chloroacetamido group of the fluorescein diester as shown below:

Due to the potential for deacylation by the amino group of the glucose amine, the reaction is preferably conducted at a temperature of from –40° C. to about 20° C. The reaction is conducted in an inert solvent such as methylene chloride, chloroform, ethyl acetate, toluene, DMF and the like in the presence of a suitable base such as diisopropylethylamine to scavenge the acid generated. Alternatively, the reaction can be conducted in pyridine. The reaction continues until substantial completion which typically occurs within 1 to 24 hours. The product is recovered and purified by conventional techniques such as chromatography, crystallization, HPLC and the like.

Alternatively, a hydroxyl-L-amine of the formula $NH_2$-L-OH can be used in the reactions above with the isothiocyanate fluorescein diester. The amino group of the hydroxyl-L-amine will react with the carboxyl group on pteroic acid or with a carboxyl group on folic acid to provide for the corresponding amide alcohol [—C(O)NH-L-OH]. The alcohol then reacts with the isothiocyanate group to provide for a thiocarbamate linkage of the folic acid or pteroic acid moiety or component to the fluorescein diester moiety or component. In these reactions, L is a linker as defined above.

Preferred compounds of the formula $NH_2$-L-OH and $NH_2$-L-$NH_2$ include those where L is a polyoxyalkylene or an alkylene group. Compounds such as $NH_2$-L-OH or $NH_2$-L-$NH_2$ are commercially available as Jeffamines (Huntsman Corp.) or from Sigma-Aldrich, supra.

Other reaction schemes to couple the reactive functionalities of the compounds of this invention with cellular targeting agents are well known. For example, amino groups on the lysine residues of antibodies can react with a —COOH, —N=C=S or —N=C=O group as per above. Carboxyl residues on aspartic and glutamic acid can react with the amino group on 5-amino fluorescein diesters.

Methods

The compounds of this invention are non-fluorescent by virtue of locking the fluorescein component into a non-fluorescent tautomeric structure due to diesterification of both phenolic hydroxyl groups. Deacylation of one or both of the ester groups restores the ability of these compounds to fluoresce.

In one embodiment, the compounds of this invention are suitable for use in detecting cancer cells from a viable excised tissue mass that preferentially absorb these compounds in greater preponderance than normal cells. For example, it is literature recognized that cervical, ovarian, brain, mesothelioma, breast, colorectal, renal, epithelial, and lung cancers all overexpress folic acid receptors. Likewise, the compounds of formula II having a pteroic acid component can be used in place of folic acid to assess the presence of such cancer cells in a cellular composition. This is because these compounds are non-fluorescent and provide no background fluorescence and further because pteroic acid will be absorbed via the folate receptors on cancer cells. Moreover, when intracellularly absorbed into the cancer cell by the folic acid receptors, intracellular enzymes such as esterases and lipases deacylate the ester group(s) of the compounds thereby converting them from non-fluorescent to fluorescent. Such allows the clinician to immediately recognize the presence of such cancer cells due to their unambiguous fluorescence. Still further, the clinician can employ the compounds of formula III as the glucosamine component is recognized by glucose receptors on cancer cells.

In one embodiment, the methods of this invention are advantageously used to identify cancer cells in an excised tissue sample. In this embodiment, an aqueous composition is applied to the tissue surface comprising viable cells using compounds that are preferentially absorbed by cancer cells. The cellular uptake of these compounds will result in the cancer cells becoming unambiguously fluorescent. In one embodiment, the aqueous composition assists in maintaining the viability of cells in the excised tissue mass or sample. Such compositions are well known in the art. In one embodiment, the so tested tissue sample can then be fixed with formaldehyde and sent to a pathologist to confirm the diagnosis made by the methods described herein.

EXAMPLES

The following non-limiting examples are provided to illustrate the claimed invention and not to provide any limitations thereto.

In the following examples, the following terms have the following definitions. If a term is undefined, it has its accepted scientific meaning.

DCC=dicyclohexylcarbodiimide
DMAP=dimethylaminopyridine
DMF=N,N-dimethylformamide
eq.=equivalent
FBS=fetal bovine serum
g=grams
mg=milligrams
mL=milliliters
mm=millimeters
RPMI=Roswell Park Memorial Institute Medium
TLC=thin layer chromatography
v/v=volume to volume Example 1—Synthesis of Methoxyethoxycarbonylproprionic Acid (Compound 12) (Scheme 1)

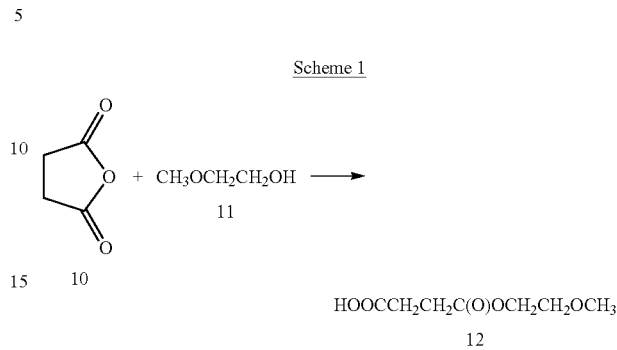

The above reaction follows the literature preparation described by J. Materials Chemistry, 2014, 2(26):4142-4145. Specifically, a slight excess of succinic anhydride was combined with 2-methoxyethanol in methylene chloride in a flask at about 20° C. A solution of triethylamine in methylene chloride was added dropwise over about a 15 minute period during which the reaction produced sufficient heat so that the solvent began to boil. Afterwards, the addition of triethylamine was stopped and the reaction stirred overnight after returning to room temperature.

The reaction was stopped and the reaction solution washed with brine and the organic layer was recovered. The solvent was stripped and the resulting product was purified by column chromatography (silica gel using a gradient of from 0 to 10% methanol in methylene chloride). The resulting product (compound 10) was used as is without further purification or isolation.

Example 2—Synthesis of the Fluorescein Diester, Compound 14 (Scheme 2)

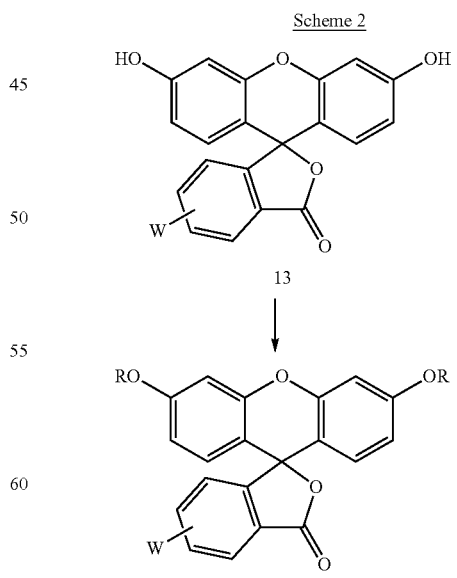

Approximately 1 equivalent of compound 12 was dissolved in methylene chloride and then combined with approximately 1 equivalent of DCC at room temperature. The mixture was stirred for approximately 5 minutes and then 0.25 equivalents of DMAP and approximately 0.25 equivalents of fluorescein 5-isothiocyanate (W is —N=C=S) were added thereto. The reaction mixture was then sonicated at 26° C. until the suspension was substantially dissipated which occurred over an approximate 15 minute period. The resulting reaction mixture was stirred overnight at room temperature and monitored for reaction completion by TLC. Upon substantial reaction completion, the non-soluble components were filtered and the resulting solution was placed on a silica column for purification purposes. The column was eluted with a solvent gradient starting at 0% methanol and 100% methylene chloride and finishing with 10% methanol and 90% methylene chloride (v/v). The elutant containing the desired compound was stripped of solvent and the resulting compound 14 was substantially free of fluorescence indicative of formation of diester. The water solubility of the compound was evaluated and assessed to be at least 10 mg/mL. A small aliquot of the compound was contacted with a sodium hydroxide solution that immediately provided for fluorescence indicative of deacylation.

Example 3—Synthesis of the Folic Acid—Fluorescein Diester Conjugate, Compound 23

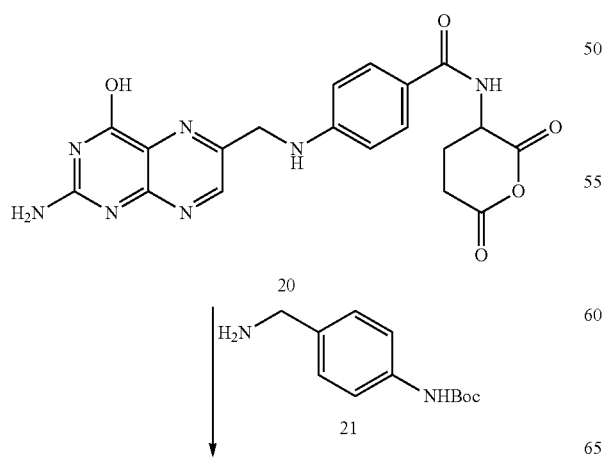

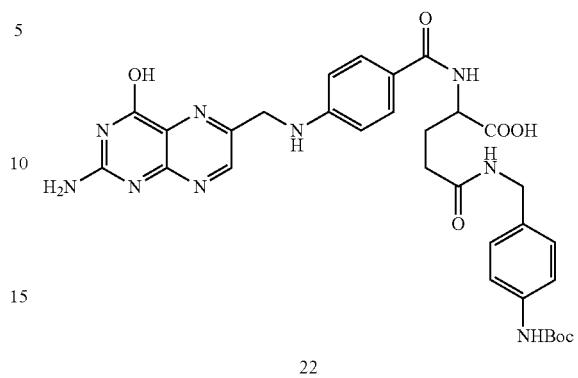

22

Compound 20 was prepared according to the literature as set forth in Guaranga, et al., Bioconjugate Chemistry, 2012, 23:84-96. In particular, compound 20 was prepared from folic acid by addition of about 6 equivalents of DCC in a solution of about 4:1 DMF:pyridine. The reaction was maintained at room temperature overnight. The solution was filtered or centrifuged to removed solids and the resulting solution containing compound 20 was combined with approximately 1 equivalent of compound 21. The reaction was maintained at room temperature overnight and the resulting solution was filtered again to remove additional solids to provide containing compound 22.

Alternatively, the reaction can be conducted by combining folic acid, DCC and compound 21 into a single reaction to provide for compound 22 where, again, solids are removed by centrifugation or filtration.

Compound 22 was optionally combined with methanol to provide for the methyl ester—compound 22 A. The Boc protecting group was removed by conventional methods and the resulting compound 22B (not shown) was combined with compound 14 in DMF at room temperature overnight so as to provide for compound 24.

compound 22 B

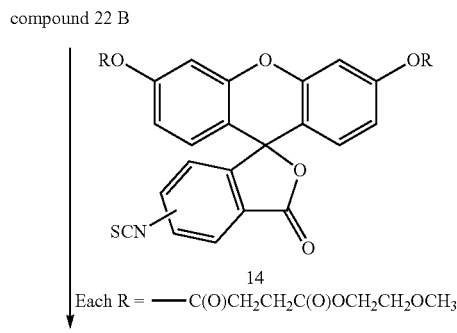

14
Each R = —C(O)CH$_2$CH$_2$C(O)OCH$_2$CH$_2$OCH$_3$

-continued

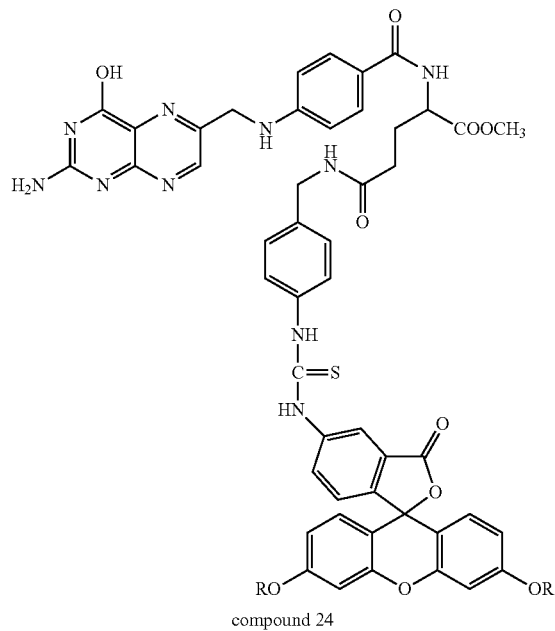

compound 24

Specifically, compound 14 was combined with compound 22B under conditions wherein the aromatic amino group reacted with the isothiocyanate to provide for compound 24.

Exemplary compounds that can be made by the methods described herein include the following:

Comparative Compound A each R is hydrogen

Comparative Compound A

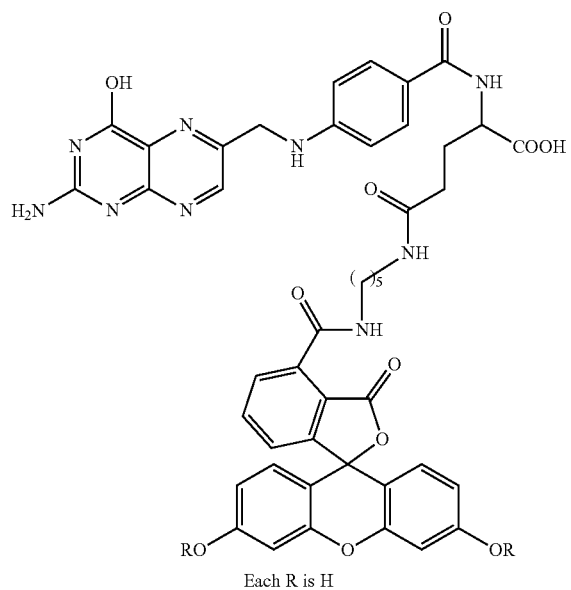

Each R is H

Compound 24—Each R is $CH_3OCH_2CH_2OC(O)CH_2CH_2C(O)$—

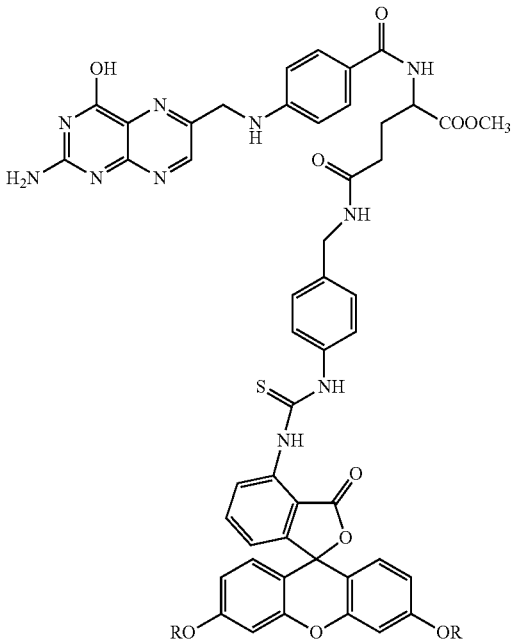

Compound 25—Each R is $CH_3OCH_2CH_2OC(O)CH_2CH_2C(O)$—

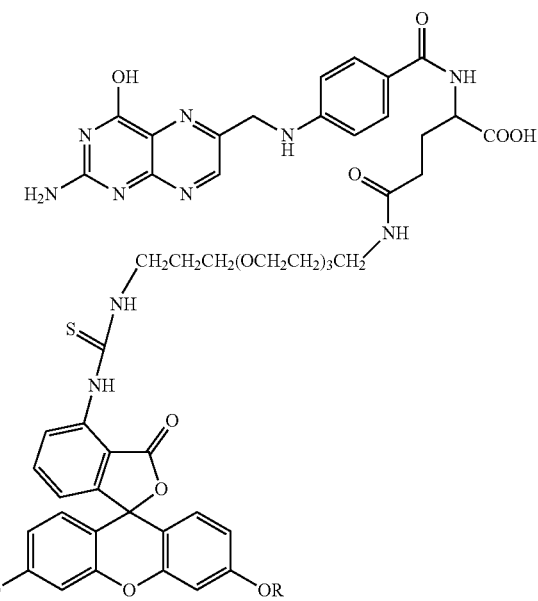

Compound 26—Each R is CH$_3$OCH$_2$CH$_2$OC(O)CH$_2$CH$_2$C(O)—

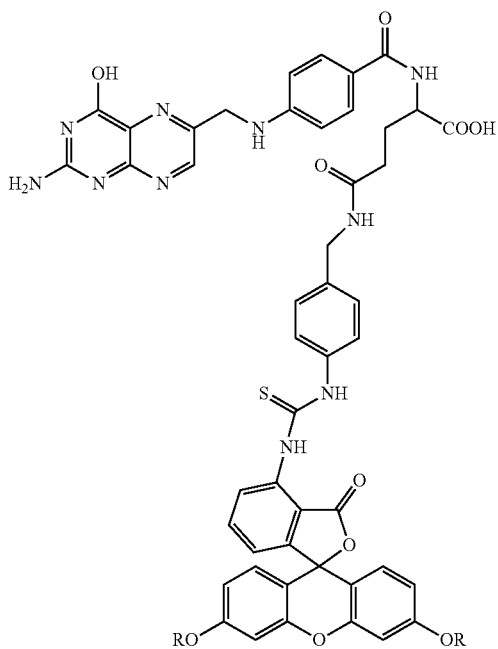

Biology

Compound 24 and comparative compound A were evaluated for their ability to be absorbed by cancer cells and then, in the case of compound 24, deacylated by intracellular esterases so as to regenerate a fluorescent structure. Specifically, approximately 500,000 SDOV3 cells (an ovarian cancer cell line) were seeded into separate 35 mm culture dishes containing a folate-free growth medium (RPMI+10% FBS—fetal bovine serum). The next day, the medium was replaced with a folate-free medium (no FBS). In one culture dish, the medium was supplemented with 25 micromolar of compound 24; and, in another culture dish, the medium was supplemented with 50 micromolar of comparative compound A. After incubation, the cells were washed with HBSS (Hank's balanced salt solution) to remove unbound compound. The cells were then imaged with a 20× immersion objective on a standard upright fluorescent microscope. In the case of compound 24, the fluorescent signal was clear, consistent and unambiguous evidencing that cancer cells were fluorescent and that the fluorescent signal was not evident in the solution. FIG. 1 shows the fluorescence generated. Note that only the cancer cells evidenced fluorescence and that the solution remained non-fluorescent.

These results establish that compound 24 targeted cancer cells, were absorbed by cancer cells, and were deacylated by intracellular enzymes. The persistent signaling solely in the cancer cells evidenced that deacylated compound 24 did not efflux from the cancer cells. On the other hand, comparative compound A also was absorbed by the cancer cells and immediately fluoresced but that was followed by loss of fluorescence likely due to bleaching under the intense light used.

Taken together, the compounds of this invention are suitable for use in detecting cancer cells.

What is claimed is:

1. A device comprising a biopsy needle and a chamber capable of receiving a biopsied tissue wherein the needle and the chamber are integrated into the device so that the biopsied tissue is fed directly from the needle into the chamber wherein the chamber contains a solution comprising a conjugate of Formula I

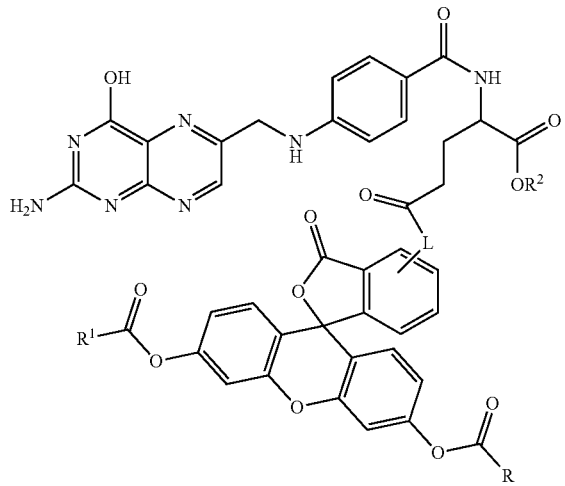

or Formula II

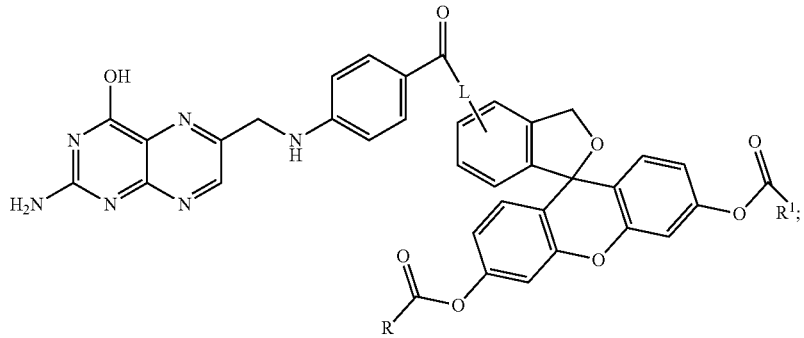

wherein R and R$^1$ are independently C$_2$-C$_{18}$ alkyl or cycloalkyl groups, wherein the C$_2$-C$_{18}$ alkyl or the cycloalkyl group also contain 1 to 8 heteroatoms selected from the group consisting of oxygen, S(O)$_x$, >$NR^3$, —OP(O)$_y$H, OS(O)$_z$H, —C(O)—, amino, $C_1$-$C_6$ alkylamino, di($C_1$-$C_6$alkyl)amino, —C(O))—, —C(O)$NR^3$, —C(O)OH, —OH, and oxo; $R^2$ is H or $CH_3$; and L is a linker of from 1 to 20 carbon atoms and 1 to 6 heteroatoms selected from the group consisting of oxygen, S(O)$_x$, >$NR^3$, —OP(O)$_y$H, —OS(O)$_z$H, —C(O)—, amino, $C_1$-$C_6$ alkylamino, di($C_1$-$C_6$alkyl)amino, —C(O)O—, —C(O)$NR^3$, —C(O)OH, —OH, and oxo, wherein y and z are independently 1 or 2 and x is 0, 1 or 2;

or pharmaceutically acceptable salts, tautomers, and/or solvates thereof of the compound of Formula I or Formula I; and further wherein said chamber is otherwise substantially non-fluorescent.

2. The device of claim 1, wherein the chamber is equipped with an external UV source and a camera capable of recording fluorescence generated by the biopsied tissue.

3. The device of claim 1, wherein the biopsied tissue contains folate dependent cancer cells.

\* \* \* \* \*